(12) United States Patent
Rota et al.

(10) Patent No.: US 9,113,980 B2
(45) Date of Patent: Aug. 25, 2015

(54) INSTRUMENT FOR DRILLING DENTAL ROOT CANALS

(75) Inventors: Gilbert Rota, Vaux et Chantegrue (FR); Paul-Henri Vallotton, Pampigny (CH)

(73) Assignee: MAILLEFER INSTRUMENTS HOLDING SARL, Ballaigues (CH)

( * ) Notice: Subject to any disclaimer, the term of this patent is extended or adjusted under 35 U.S.C. 154(b) by 0 days.

(21) Appl. No.: 13/988,795

(22) PCT Filed: Feb. 12, 2011

(86) PCT No.: PCT/IB2011/002913
§ 371 (c)(1),
(2), (4) Date: May 22, 2013

(87) PCT Pub. No.: WO2012/073106
PCT Pub. Date: Jun. 7, 2012

(65) Prior Publication Data
US 2013/0244200 A1  Sep. 19, 2013

(30) Foreign Application Priority Data

Dec. 3, 2010 (EP) ..................................... 10015255

(51) Int. Cl.
*A61C 5/02* (2006.01)
(52) U.S. Cl.
CPC ..................................... *A61C 5/023* (2013.01)
(58) Field of Classification Search
CPC .......... A61C 5/023; A61C 3/02; A61C 3/025; A61C 3/03; A61C 3/08
USPC ................................. 433/102, 165
See application file for complete search history.

(56) References Cited

U.S. PATENT DOCUMENTS

| 5,762,497 | A | * | 6/1998 | Heath ........................... 433/102 |
| 5,873,719 | A | | 2/1999 | Calas et al. |
| 7,322,105 | B2 | * | 1/2008 | Lewis .......................... 29/896.1 |
| 7,398,598 | B2 | * | 7/2008 | Lewis et al. .................. 29/896.1 |

(Continued)

FOREIGN PATENT DOCUMENTS

| CN | 2815300 Y | 9/2006 |
| CN | 2917573 Y | 7/2007 |
| EP | 0 801 930 A1 | 10/1997 |

OTHER PUBLICATIONS

International Search Report, dated Feb. 2, 2012, from corresponding PCT application.

(Continued)

*Primary Examiner* — Cris L Rodriguez
*Assistant Examiner* — Hao D Mai
(74) *Attorney, Agent, or Firm* — Young & Thompson

(57) ABSTRACT

An instrument for drilling dental root canals, includes a tapered rod having on at least an active part of its length, at least one helical flute defining at least one helical cutting edge. The instrument also has a helical hollow on a portion of the active part extending as far as the point of the rod. At least one of the edges defined by the helical hollow is coincident with the cutting edge, the hollow reducing the cutting angle of the cutting edge. Any cross-section of the active part has at least one convex side belonging to the helical flute. The closer the cross-section in question is to the point of the rod, the more the curvature at any point of the convex side increases and tends to approximate the curvature of the circumscribed circle of the cross-section and passing via the cutting edge defined by the helical flute.

3 Claims, 3 Drawing Sheets

(56) References Cited

U.S. PATENT DOCUMENTS

| | | |
|---|---|---|
| 2004/0043357 A1* | 3/2004 | Garman ................. 433/102 |
| 2005/0272004 A1* | 12/2005 | Desrosiers ............ 433/102 |
| 2005/0282108 A1 | 12/2005 | Goodis |
| 2006/0210947 A1* | 9/2006 | Lampert ................ 433/102 |
| 2010/0297578 A1 | 11/2010 | Jaunberzins |

OTHER PUBLICATIONS

Chinese Search Report, corresponding to CN Patent Application CN2011858310 20111202.

* cited by examiner

INSTRUMENT FOR DRILLING DENTAL ROOT CANALS

BACKGROUND OF THE INVENTION

1. Field of the Invention

The present invention relates to an instrument for drilling dental root canals.

2. Description of the Related Art

The treatment of an infected dental root is effected by extracting the pulp with the aid of appropriate instruments, then by shaping the root canal by successive drilling operations, traditionally carried out with the aid of instruments of varying size and conicity. The final operation consists of filling the root canal.

The shaping of the root canal consists initially of enlarging the canal in its crown and median parts in order subsequently to permit easier treatment of the apical part of the canal by mechanical cleaning of the infected tissues.

An instrument designed for drilling dental root canals generally has a tapering rod fitted into a handle to permit it to be moved manually or mechanically and having helical flutes on at least a part of its length, which flutes have a pitch which may or may not be constant, and having at least one cutting edge.

When being used in continuous rotation, this type of instrument can tend to screw itself into the canal. EP 0 801 930 describes a dental reamer enabling this screwing problem to be avoided and being characterised in that the tangent to the cutting point of the instrument tends to be superimposed with the tangent to the diameter of the circle in which a cutting cross-section is inscribed and passing via the said cutting point.

U.S. 2005/0282108 describes an endodontic file including a file body extending from a tip region to a shank region and at least one helical flute having a cutting edge and extending from the tip region towards the shank region. In one embodiment, the file according is characterised by the fact that the clearance angle defined by the cutting edge varies between the tip region and the shank region of the file and in particular decreases from the shank region to the tip region. The smaller the clearance angle the greater the forces, and especially the friction forces exerted on the file. However, in the disclosed embodiment, the decreasing of the clearance angle leads to a decreasing of the convexity of the convex portion of the flute which in turn leads to a loss of strength of the file. This could therefore lead to a file having reduced strength especially in the tip portion. In another embodiment, the file is characterised in that the flute depth measuring the deepest portion of the flute is not constant along the entire working portion of the endodontic file, but rather decreases from the shank portion to the tip portion. The decrease of the flute depth allows reinforcing the file at its point where it is the most fragile and where the forces and torsional stress are the greatest. However, the decrease of the flute depth leads to a decrease in the effectiveness of the cutting edge, particularly at the tip. Thus, with this embodiment, a file with improved strength but less effectiveness is obtained.

Apart from the screwing problem, another problem arising in the production of instruments for drilling root canals is that of the strength and flexibility of the instruments. In fact, when the instrument is too flexible it may bend over or break before the practitioner has been able to terminate the operation, and when the instrument is too rigid, it follows the curvature of the dental root canal only with difficulty.

Similarly the effectiveness of a cutting edge is assessed at its cutting angle. When considering a cross-section of an instrument inscribed in a circumscribed circle passing via its cutting edges, the cutting angle of a cutting edge of the instrument is defined as the angle between a diameter of the circumscribed circle of the cross-section passing via the cutting edge and the tangent to the side of the cross-section having as its vertex the said cutting edge (the said side is determined according to the direction of rotation of the helical flutes of the instrument). The more acute the cutting angle of a cutting edge (even negatively), the greater the effectiveness of the said edge. However, in general the more acute the cutting angle, the more acute is the angle at the vertex of a cutting edge, i.e. the finer and more fragile the cutting edge, which means that the instrument which becomes thinner towards its point also becomes more fragile. However, it is at the point of the instrument that the forces and torsion are the greatest. It is therefore also necessary to take into account the effectiveness of an instrument and to find a compromise between effectiveness, flexibility and strength.

BRIEF SUMMARY OF THE INVENTION

The aim of the present invention is to produce an instrument permitting a good level of effectiveness without excessively weakening the said instrument.

The present invention relates to an instrument for drilling dental root canals, comprising a tapered rod having on at least a part of its length, constituting its active part, at least one helical flute defining at least one helical cutting edge, and a helical hollow on a portion of the said active part of the rod extending as far as the point of the rod, characterised in that at least one of the edges defined by the said at least one helical hollow meets the cutting edge defined by the said at least one helical flute, the said hollow reducing the cutting angle of the said cutting edge; in that any cross-section of the active part of the rod has at least one convex side belonging to the helical flute; and in that the closer the cross-section in question is to the point of the rod, the more the curvature at any point of the said convex side increases and tends to approximate the curvature of the circumscribed circle of the said cross-section and passing via the cutting edge defined by the said helical flute.

In the following, a planar geometric figure is described as convex if it fulfils the criterion that for any pair of points of the figure the segment connecting them is entirely contained within the said figure. A side of a geometric figure is described as convex if this side is at any point curved towards the outside of the said geometric figure, and is described as concave if this side is at any point curved towards the inside of the geometric figure.

The curvature of a geometric object is a quantitative measurement of the "more or less curved" character (i.e. more or less convex or more or less concave depending on the orientation) of this object. For example, in the Euclidian plane a straight line is an object with a zero curvature, and a circle is an object with constant positive curvature. The curvature of an arc at a point of the said arc is defined as the curvature of the unique circle tangential to the arc at this point.

BRIEF DESCRIPTION OF THE DRAWINGS

An embodiment of the instrument according to the invention is schematically illustrated by way of example in the drawings in which.

DETAILED DESCRIPTION OF THE PREFERRED EMBODIMENTS

Figure 1:
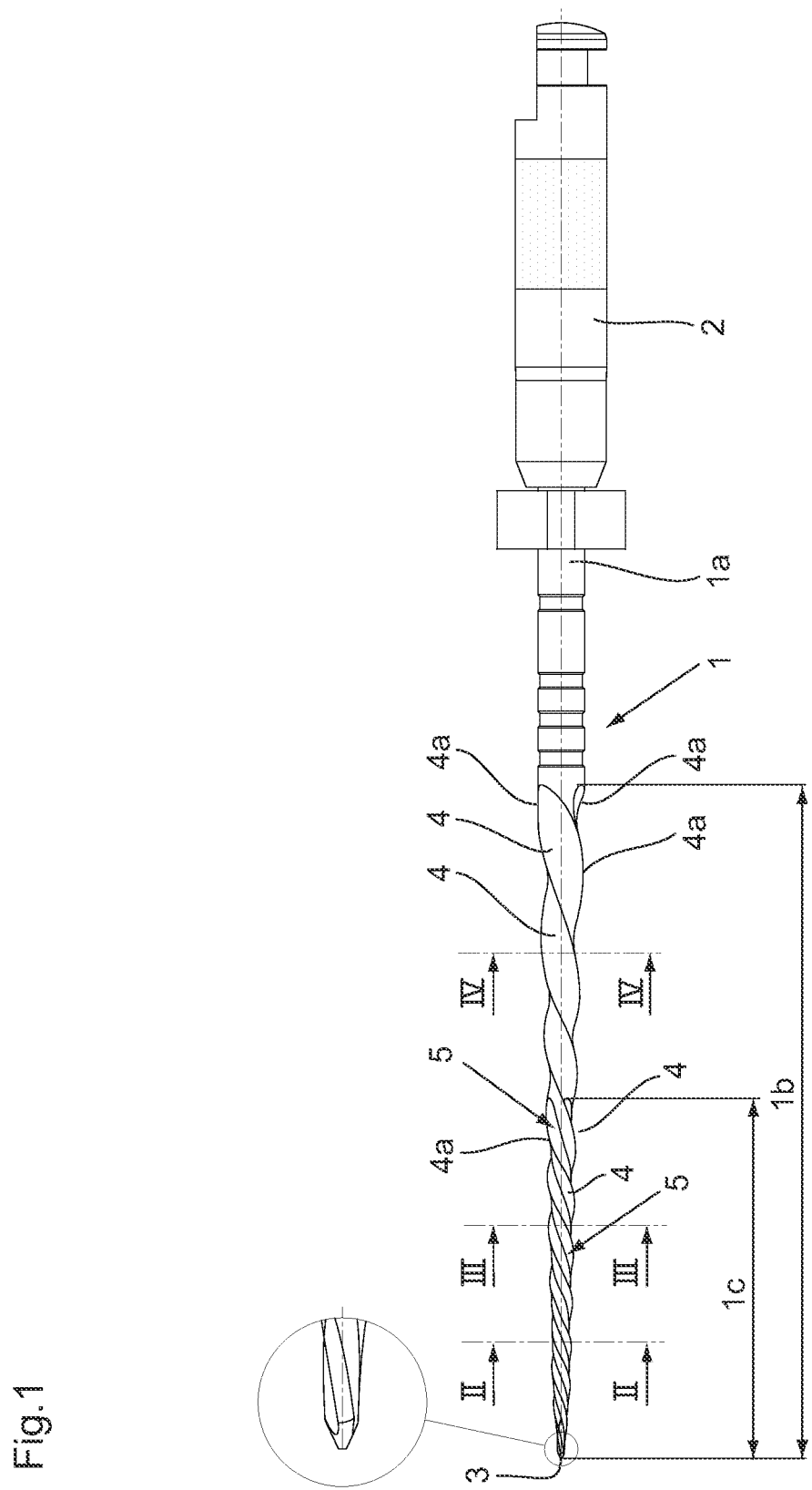
FIG. 1 illustrates an instrument for drilling dental root canals according to the invention.

The instrument according to the invention illustrated in FIG. 1 comprises a rod 1 fitted at one of its ends 1a in a handle 2 permitting either manual actuation of the instrument or, preferably, its engagement in a hand piece ensuring mechanical driving of the said instrument.

The said rod 1 has an active part 1b extending to the other end 3, termed the tip 3, of the rod 1. The said active part 1b is tapered and conical, becoming thinner to the tip 3 of the rod 1.

In the illustrated embodiment, the active part 1b of the rod 1 has, over its entire length, three helical flutes 4 each defining a cutting edge 4a. The active part 1b consequently has an essentially triangular cross-section 6, each of the sides 6a of which define/belong to a helical flute 4 and each of the three vertices 6b define/belong to a cutting edge 4a. According to the present invention and as illustrated in FIG. 4, the cross-section 6 is a convex figure and each of its three sides 6a is convex, i.e. curved towards the outside of the said cross-section.

According to the invention, the closer a cross-section 6 is to the tip 3 of the rod 1, the greater the convexity of the sides 6a of the said cross-section, i.e. the more their curvature at any point tends to approximate the curvature of the circumscribed circle C6 of the cross-section 6 and passing via the vertices 6b of the said cross-section. Hence, as seen in the figures, the closer a cross section 6 is to the tip 3 of the rod 1, the greater is the curvature of the sides 6a of the said cross section 6. The curvature of the sides 6a thus increases towards the tip.

Figure 4:
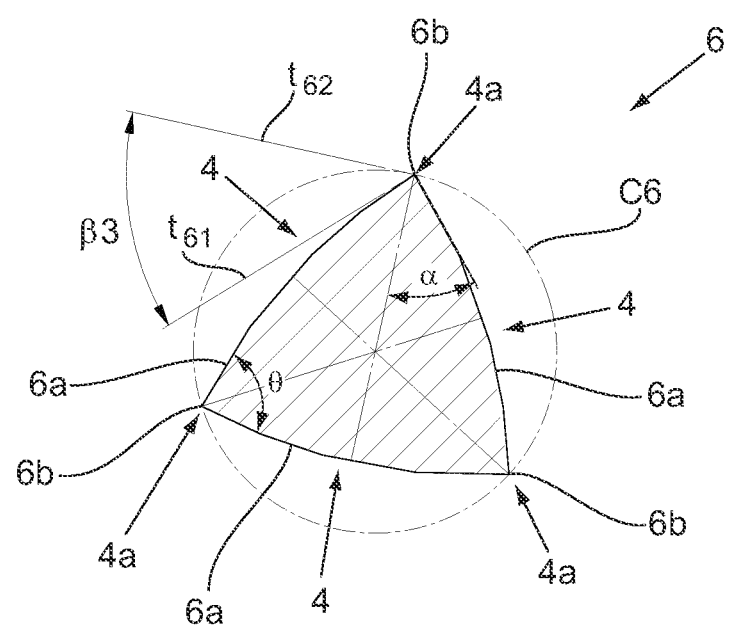
FIG. 4 is a cross-sectional view along the line IV-IV of the instrument illustrated in FIG. 1.

The curvature of a side 6a of a cross-section 6 of the active part 1b is also illustrated, for example, in FIG. 4 by the angle β3 which is the angle between the tangent $t_{61}$ to a side 6a passing via a vertex 6b of the said side and the tangent $t_{62}$ to the circumscribed circle C6 of the cross-section 6 and passing via the same vertex 6b. According to the invention the angle β3 thus varies from cross-section to cross-section, becoming smaller the closer the cross-section is to the tip 3 illustrating that the curvature of the side 6a increases and tends to approximate the curvature of the circumscribed circle C6 of the cross section 6 and passing via the vertex 6b.

The active part 1b of the rod 1 has, on a part of its length, a cutting portion 1c extending to the tip 3. In the illustrated embodiment the cutting portion 1c has, over its whole length, three helical hollows 5 in addition to the three helical flutes 4. Each hollow 5 defines two edges 5a, 5b, at least one of which is coincident with a cutting edge 4a. Each hollow 5 reduces the cutting angle of a cutting edge 4a, rendering this edge more effective.

Figure 2:
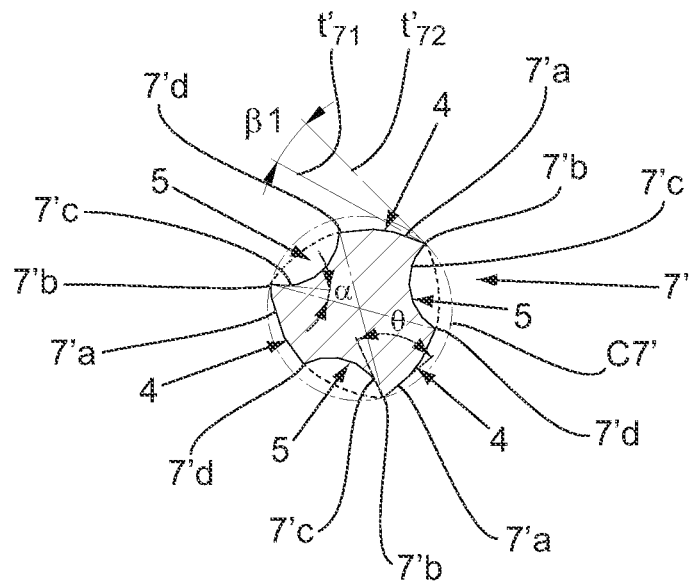
FIG. 2 is a cross-sectional view along the line II-II of the instrument illustrated in FIG. 1.
Figure 3:
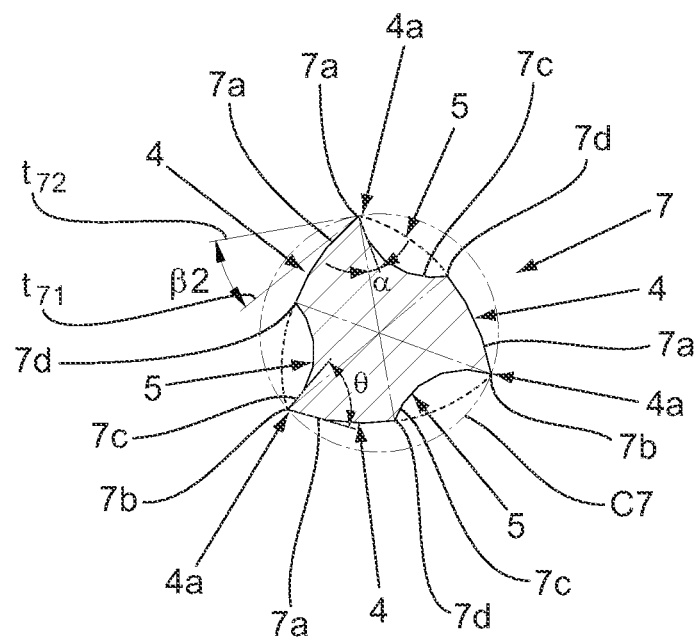
FIG. 3 is a cross-sectional view along the line of the instrument illustrated in FIG. 1.

A cross-section 7 of the cutting portion 1c which is illustrated, for example, in FIG. 3, is obtained from a triangular cross-section such as the cross-section 6 illustrated in FIG. 4 (shown in dotted lines in FIGS. 2 and 3) which has hollows 5 produced in its sides 6a. A cross-section 7 of the cutting portion 1c is thus a non-convex polygon having six sides: three first sides 7a each defining/belonging to a helical flute 4 and three second sides 7c each defining/belonging to a helical hollow 5. The cross-section 7 also has six vertices: three first vertices 7b (corresponding to the vertices 6b of a cross-section 6 illustrated in FIG. 4) each defining/belonging to a cutting edge 4a, and three second vertices 7d.

As for the cross-section 6 described above, the first three sides 7a are convex, whereas the three second sides 7b are concave, i.e. curved towards the inside of the cross-section 7.

In the illustrated embodiment each first vertex 7b is the vertex of a first side 7a and of a second side 7c.

Furthermore, according to the invention and as described in relation to the cross-section 6, the convexity of the first sides 7a increases the closer the cross-section 7 in question is to the tip 3. More precisely, the curvature at any point of the said first sides 7a tends to approximate the curvature of the circumscribed circle C7 of the cross-section 7 and passing via all the cutting edges 4a, i.e. via all the first vertices 7b. Hence, as seen in the figures, the closer a cross section 7 is to the tip 3 of the rod 1, the greater is the curvature of the first sides 7a of the said cross section 7. The curvature of the first sides 7a thus increases towards the tip 3.

FIG. 2 illustrates a posterior cross-section 7' of the cutting portion 1c of the active part 1b of the rod 1 which is closer to the tip 3 than the cross-section 7 illustrated in FIG. 3. The references relating to the cross-section 7 followed by a prime symbol will be used to describe this posterior cross-section 7'.

This posterior cross-section 7' is of the same form and has the same features as the cross-section 7 described above. In particular, the first three sides 7'a of the cross-section 7' are convex. According to the invention, the convexity of the said first sides 7'a of the said posterior cross-section 7' is greater than the convexity of the first sides 7a of the cross-section 7 illustrated in FIG. 3 since this latter cross-section is further away from the tip 3.

This difference in convexity is illustrated in the figures by the angles β2 and β1. The angle β2 is the angle between the tangent $t_{71}$ to a first side 7a passing via a first vertex 7b and the tangent $t_{72}$ to the circumscribed circle C7 of the cross-section 7 passing via the said same vertex 7b. The said angle β2 thus illustrates the curvature of the first side 7a. Similarly, the curvature of a side 7'a of the posterior cross-section 7' is illustrated in FIG. 2 by the angle β1 which is the angle between the tangent $t'_{71}$ to a first side 7'a passing via a first vertex 7'b and the tangent $t'_{72}$ to the circumscribed circle C'7 of the cross-section 7' and passing via the said first vertex 7'b. Since according to the invention the curvature of a first side 7'a of the posterior cross section 7' is greater than the curvature of a first side 7a of the cross section 7, and the convexity of the said first side 7'a of the posterior cross section 7' is greater than the convexity of the sid first side 7a of the cross section 7, the angle β2 is greater than β1.

Thus according to the present embodiment and as illustrated in FIGS. 2 to 4, each cross-section (6, 7, 7') of the active part 1b of the rod 1 has three convex first sides (6a, 7a, 7'a), a vertex (6b, 7b, 7'b) of which defines a cutting edge 4a and the convexity of these three convex sides increases the closer the cross-section in question is to the tip 3.

According to the invention, the angle β3 illustrating the curvature of the sides 6a of the cross-section 6 is thus greater than the angle β2 illustrating the curvature of the convex first sides 7a of the cross-section 7, which is itself greater than the angle β1 illustrating the curvature of the convex sides 7'a of the cross-section 7', thus showing that the convexity of the convex sides of a cross-section of the instrument in accordance with the invention increases the closer the cross-section is to the tip 3 of the said instrument.

The addition of a hollow 5 on the cutting portion 1c of the rod 1 makes it possible to increase the effectiveness of the cutting edges 4a defined over the whole length of the active part 1b of the rod 1 by the helical flutes 4. In fact, the hollows 5 reduce the cutting angle α of a cutting edge 4a, rendering it more acute (as shown in FIGS. 3 and 4). In the prior art, the addition of such hollows 5 would have the effect of also reducing the angle at the vertex θ of a cutting edge, rendering this cutting edge, and by extension the instrument, more fragile.

However, according to the present invention and as illustrated in FIGS. 2 and 3, along the cutting portion 1c of the rod 1, a cutting edge 4a is defined by a convex first side 7a, 7'a and a concave second side 7c, 7'c having as a common vertex a first vertex 7b, 7'b belonging to the said cutting edge 4a. Furthermore, and also in accordance with the invention, the convexity of the said first side 7a, 7'a increases the closer the cross-section in question is to the tip 3 of the rod 1. Thus a cutting edge 4a is obtained, the cutting angle α of which is rendered more acute by the addition of a hollow 5 but the angle of which at the vertex θ is substantially preserved by increasing the convexity of the convex first side 7a defining the cutting edge 4a.

Thus the increase in the convexity of the convex first sides 7a, 7'a makes it possible to reinforce the rod 1 towards its tip 3 and to compensate for the fragility created by the hollows 5 by compensating for the material removed from the instrument by providing the hollows. Moreover, the convexity of the first sides 7a, 7'a increases towards the tip 3 where the rod is the most fragile but also where the force and torsional stress are the greatest when the instrument is being used.

Thus an instrument for drilling dental root canals is obtained, which is effective without loss of strength.

An instrument of this type can be obtained from a rod with a circular cross-section, preferably made of a nickel titanium alloy. Helical flutes are provided therein by machining, which flutes define cutting edges such that, over the whole length of its active part, the cross-section of the rod is a polygon, the sides of which define the helical flutes and the convexity of the sides of the said polygon increases, the closer the cross-section is to the tip 3 of the rod 1, i.e. the curvature at any point of the sides tends to approximate the curvature of the circumscribed circle of the cross-section and passing via the cutting edges, the closer the said cross-section is to the tip 3 of the rod. Helical hollows are then machined on a part of the rod extending towards its point, in order to accentuate and improve the effectiveness of the cutting edges defined by the helical flutes.

The helical hollows and flutes of an instrument in accordance with the invention may or may not have a constant pitch and can turn clockwise or anticlockwise.

The instrument according to the invention can be used in continuous rotation or alternating rotation, for example 150° in one direction and 30° in the reverse direction to attenuate the screwing effect.

The present embodiment has been described by way of example only. In general, the instrument in accordance with the invention has, on an active part of its rod, at least one helical flute defining at least one cutting edge and on a portion of the active part at least one hollow having an edge in common with at least one cutting edge. Any cross-section of the active part of the rod has a convex side defining a helical flute and the convexity of which increases the closer the cross-section is to the point of the rod.

The invention claimed is:

1. An instrument for drilling dental root canals, the instrument comprising:
   a tapered rod having on at least a part of a length thereof, constituting an active part, at least one helical flute defining at least one helical cutting edge, and at least one helical hollow on a portion of the active part of the rod extending to a point of the rod, at least one of edges defined by the at least one helical hollow is coincident with the cutting edge defined by the at least one helical flute, the helical hollow reducing a cutting angle of the cutting edge,
   wherein any cross-section of the active part of the rod has at least one convex side belonging to the helical flute, and
   the closer the cross-section is to the point of the rod, the more a curvature at any point of the convex side increases and tends to approximate a curvature of a circumscribed circle of the cross-section and passes via the cutting edge defined by the helical flute, the curvature at any point of the convex side being smaller than the curvature of the circumscribed circle of the cross-section,
   wherein an angle between a tangent to the convex side passing via a vertex of the convex side and a tangent to the circumscribed circle of the cross-section passing the vertex of the convex side progressively decreases the closer the cross-section is to the point of the rod.

2. The instrument as claimed in claim 1, wherein the active part of the rod has three helical flutes defining three cutting edges.

3. The instrument as claimed in claim 2, wherein the active part has, on a part of a length thereof, three hollows each having an edge which is coincident with the cutting edge.

* * * * *